US008449601B2

(12) United States Patent
Weber

(10) Patent No.: US 8,449,601 B2
(45) Date of Patent: May 28, 2013

(54) MEDICAL DEVICES

(75) Inventor: Jan Weber, Maple Grove, MN (US)

(73) Assignee: Boston Scientific Scimed, Inc., Minneapolis, MN (US)

( * ) Notice: Subject to any disclaimer, the term of this patent is extended or adjusted under 35 U.S.C. 154(b) by 2514 days.

(21) Appl. No.: 10/299,466

(22) Filed: Nov. 19, 2002

(65) Prior Publication Data

US 2004/0098089 A1 May 20, 2004

(51) Int. Cl.
*A61F 2/82* (2006.01)

(52) U.S. Cl.
USPC ............... 623/1.34; 623/1.49; 623/23.71

(58) Field of Classification Search
USPC .......... 623/1.44–1.54, 1.1, 1.34, 1.42, 1.49; 623/23.64–23.71; 424/9.3, 9.322, 422, 423; 606/12
See application file for complete search history.

(56) References Cited

U.S. PATENT DOCUMENTS

| | | | |
|---|---|---|---|
| 5,195,969 A | 3/1993 | Wang et al. | |
| 5,270,086 A | 12/1993 | Hamlin | |
| 5,366,504 A | 11/1994 | Andersen et al. | |
| 5,674,242 A | 10/1997 | Phan et al. | |
| 5,693,085 A * | 12/1997 | Buirge et al. | 623/1.13 |
| 5,780,807 A | 7/1998 | Saunders | |
| 5,824,037 A * | 10/1998 | Fogarty et al. | 623/1.13 |
| 6,428,571 B1 | 8/2002 | Lentz et al. | |
| 6,645,626 B2 * | 11/2003 | Garcia et al. | 428/402 |
| 2003/0004563 A1 * | 1/2003 | Jackson et al. | 623/1.15 |

FOREIGN PATENT DOCUMENTS

| | | |
|---|---|---|
| DE | 2 152 142 | 10/1971 |
| EP | 0756853 A1 * | 6/1996 |
| WO | WO 99/32051 | 7/1999 |
| WO | WO 02/083194 | 10/2002 |
| WO | WO 02/083223 | 10/2002 |

OTHER PUBLICATIONS

Templin, M. et al. "Organically Modified Alununosilicate Mesostructures from Block Copolymer Phases", Science, vol. 278, 1795-1798, Dec. 5, 1997.*
Craig, Charles H., et al., U.S. Appl. No. 10/112,391, "Platinum Enhanced Alloy and Intravascular or Implantable Medical Devices Manufactured Therefrom" filed Mar. 28, 2002.
Mendes, M.; Oliveria, V.; Vilar, R.; Beinhorn, F.; Ihlemann, J.; Conde, O.; "Femtosecond Ultraviolet Laser Micromachining of $Al_2O_3$—TiC ceramics", *Journal of Laser Applications*, vol. II, No. 5, pp. 211-215, Oct. 1999.
Stinson, Jonathan, U.S. Appl. No. 10/229,548, "Medical Devices and Methods of Making the Same" filed Aug. 8, 2002.
Templin, M.; Franck, A.; Du Chesne, A.; Leist, H.; Zhang, Y.; Ulrich, R.; Schädler, V.; Wiesner, U.; "Organically Modified Aluminosilicate Mesostructures from Block Copolymer Phases", *Science*, vol. 278, pp. 1795-1798, Dec. 5, 1997.
Weber, Jan, U.S. Appl. No. 09/724,503, "Method for Manufacturing a Medical Device Having a Coated Portion by Laser Ablation", filed Nov. 28, 2000.
Weber, Jan, U.S. Appl. No. 10/216,988, "Tunable MRI Enhancing Device", filed Aug. 12. 2002.
Zhong, Sheng-Ping, et al., U.S. Appl. No. 09/895,415, "Coating a Medical Appliance With a Bubble Jet Printing Head", filed Jul. 2, 2001.
International Search Report mailed May 28, 2004.

* cited by examiner

*Primary Examiner* — David Isabella
*Assistant Examiner* — Suba Ganesan
(74) *Attorney, Agent, or Firm* — Fish & Richardson P.C.

(57) ABSTRACT

Medical devices including an organic-inorganic composite material, including methods of making the devices, are disclosed.

16 Claims, 3 Drawing Sheets

MEDICAL DEVICES

TECHNICAL FIELD

The invention relates to medical devices, such as, for example, stents and stent grafts.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon expandable endoprosthesis. The balloon can be inflated to deform and to fix the expanded endoprosthesis at a predetermined position in contact with the lumen wall. The balloon can then be deflated, and the catheter withdrawn.

In another technique, a self-expandable endoprosthesis is formed of an elastic material that can be reversibly compacted and expanded, e.g., elastically or through a material phase transition. During introduction into the body, the endoprosthesis is restrained in a compacted condition on a catheter. Upon reaching the desired implantation site, the restraint is removed, for example, by retracting a restraining device such as an outer sheath, enabling the endoprosthesis to self-expand by its own internal elastic restoring force.

To support a passageway open, endoprostheses can be made of materials, such as stainless steel (e.g., 316L (18Cr-10Ni) stainless steel) or Nitinol (a nickel-titanium alloy), having appropriate mechanical properties, such as tensile strength and yield strength.

SUMMARY

The invention relates to medical devices, such as, for example, stents and stent grafts.

In one aspect, the invention features s medical device including a body including an organic portion, and an inorganic portion distinct from the organic portion.

In another aspect, the invention features a medical device including a body having a mesostructure having an organic portion, and an inorganic portion distinct from the organic portion.

Embodiments of aspects of the invention may include one or more of the following features. The body includes a plurality of organic portions and a plurality of inorganic portions distinct from the organic portions, and the inorganic portions are in an ordered array. The inorganic portions and/or the organic portions are lamellar. The inorganic portions are substantially cylindrical. The inorganic portions are arranged in a hexagonal array. The inorganic portions include a metallic element, such as, for example, silicon or aluminum. The inorganic portions include a three-dimensional network of metallic elements connected by bridging elements, such as, for example, oxygen.

The organic portion can include a polymer, such as, for example, a block copolymer. The organic portions can be about 5 to 100 nm long.

The body can include a therapeutic agent. The body can include an adhesion enhancing material. The body can be tubular.

The device can be a stent, a stent-graft, a vascular graft, a catheter, or a medical balloon.

The body can include a plurality of organic portions and a plurality of inorganic portions distinct from the organic portions, the inorganic portions being in an ordered array.

Embodiments may have one or more of the following advantages. The device can have good biocompatibility. The device can have good mechanical properties, such as strength and creep resistance. The device can be compatible with magnetic resonance imaging. The device can include a therapeutic agent or drug. The composite material can be use to make a flexible and/or expandable medical device. The composite material can be used in a variety of medical devices.

Other aspects, features, and advantages of the invention will be apparent from the description of the preferred embodiments thereof and from the claims.

DETAILED DESCRIPTION

Figure 1:
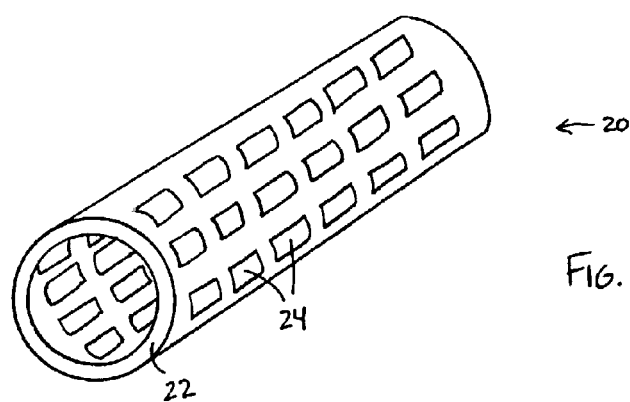
FIG. 1 is an illustration of an embodiment of a medical device.

Referring to FIG. 1, a stent 20 includes a tubular body 22 having openings 24. Tubular body 22 includes an organic-inorganic composite material. The composite material is a hybrid material capable of providing stent 20 with a combination of desirable properties. For example, an organic component of the composite material can provide stent 20 with good biocompatibility and compatibility with magnetic resonance imaging (MRI); while an inorganic component of the composite material can provide the stent with good mechanical properties, such as strength. In particular, the composite material can have relatively low magnetic susceptibility and/or relatively high electrical resistivity. As a result, the occurrence of radiofrequency artifacts can be reduced (e.g., eliminated), distortion of the magnetic field in magnetic resonance systems can be reduced (e.g., minimized), and/or an internal volume of stent 20 can be visualized.

Figure 2A:
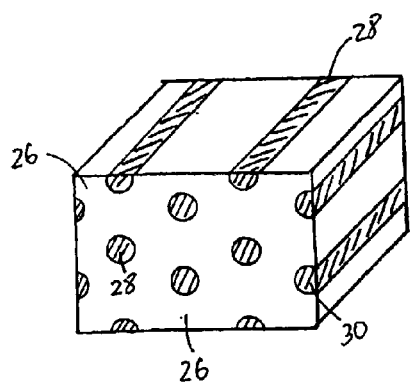
FIGS. 2A and 2B are schematic diagrams of composite materials.
Figure 2B:
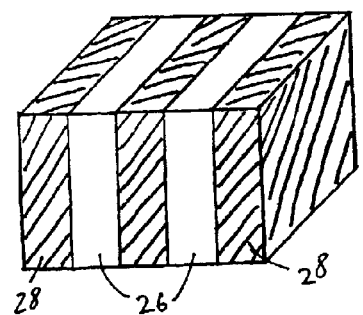

Referring to FIGS. 2A and 2B, the composite material includes organic portions 26 and inorganic portions 28. Portions 26 and 28 are arranged in an ordered array, e.g., the portions are not disordered or randomly arranged on the order of greater than several hundred nanometers. In some embodiments, portions 26 and 28 are ordered up to about 100 mn, 200 nm, 300 nm, 400 nm, 500 nm, or more. As shown in FIG. 2A, inorganic portions 28 form hexagonally arranged, substantially cylindrical portions 30 separated by organic portions 26. As shown in FIG. 2B, organic portions 26 and inorganic portions 28 form a lamellar structure having alternating layers. Other arrangements are possible. For example, portions 26 and/or 28 can form a cubic structure, an inverse hexagonal structure, a cubic bicontinuous structure (sometimes called the "plumber's nightmare"), and/or a structure having micelles. The plumber's nightmare structure can be relatively flexible.

More generally, organic and inorganic portions 26 and 28 form a mesostructure. In certain embodiments, portions 26 and 28 form a silica-type mesostructure. For example, in certain embodiments, organic portions 26 include a polymer. The polymer can be a block copolymer of relatively high molecular weight to form a mesostructure, e.g., one having a length scale on the order of the characteristic length scale of the chains, e.g., about 5 to about 100 nanometers. An example of a block copolymer is poly(isoprene-b-ethyleneoxide). Inorganic portions 28 include metal atoms such as aluminum or silicon. In some embodiments, inorganic portions 28 include metal atoms connected to other metal atoms by bridging atoms, such as oxygen, to form a three-dimensional network. Without wishing to be bound by theory, as described above, organic portions 26 can provide the composite material with flexibility, expandability, good biocompatibility, and compatibility to MRI (e.g., the portions do not interfere with MRI); while inorganic portions 28 can enhance the strength of the composite material. In particular, inorganic portions 28 can enhance the strength of the composite material without compromising the material's flexibility.

The composite material can be made by a sol-gel process including a solvent-cast technique. Poly(isoprene-b-ethyleneoxide) block copolymers (PI-b-PEO) (0.5 g) can be dissolved in a 1:1 mixture of $CHCl_3$ and tetrahydrofuran (5 weight percent polymer). Under moderate stirring, a prehydrolyzed solution of 80 mol % $(CH_3O)_3Si(CH_2)_3OCH_2CHCH_2$—O (GLYMO) and 20 mol % $Al(OBu^s)_3$ can be added, and after two hours, the mixture can be transferred to a petri dish at 333 to 343 K. After subsequent evaporation of the organic solvents (about one hour), the formation of the composite can be accomplished by heat treatment at 403 K in vacuum for 45 minutes. Films of the composite material with thicknesses of about 0.5 to 1 mm can be prepared by these procedures by adding different amounts of the metal alkoxide solution to the same block copolymer. Different structures, e.g., cubic, hexagonal, inverse hexagonal, etc, can also be prepared by varying the fraction of the polymer and/or the alkoxide.

The preceding preparation and other experimental details, including characterization of the materials, are described in Templin et al., "Organically Modified Aluminosilicate Mesostructures from Block Copolymer Phases", *Science*, Vol. 278, p. 1795 (5 Dec. 1997), and references cited therein, all of which are hereby incorporated by reference.

Figure 3:
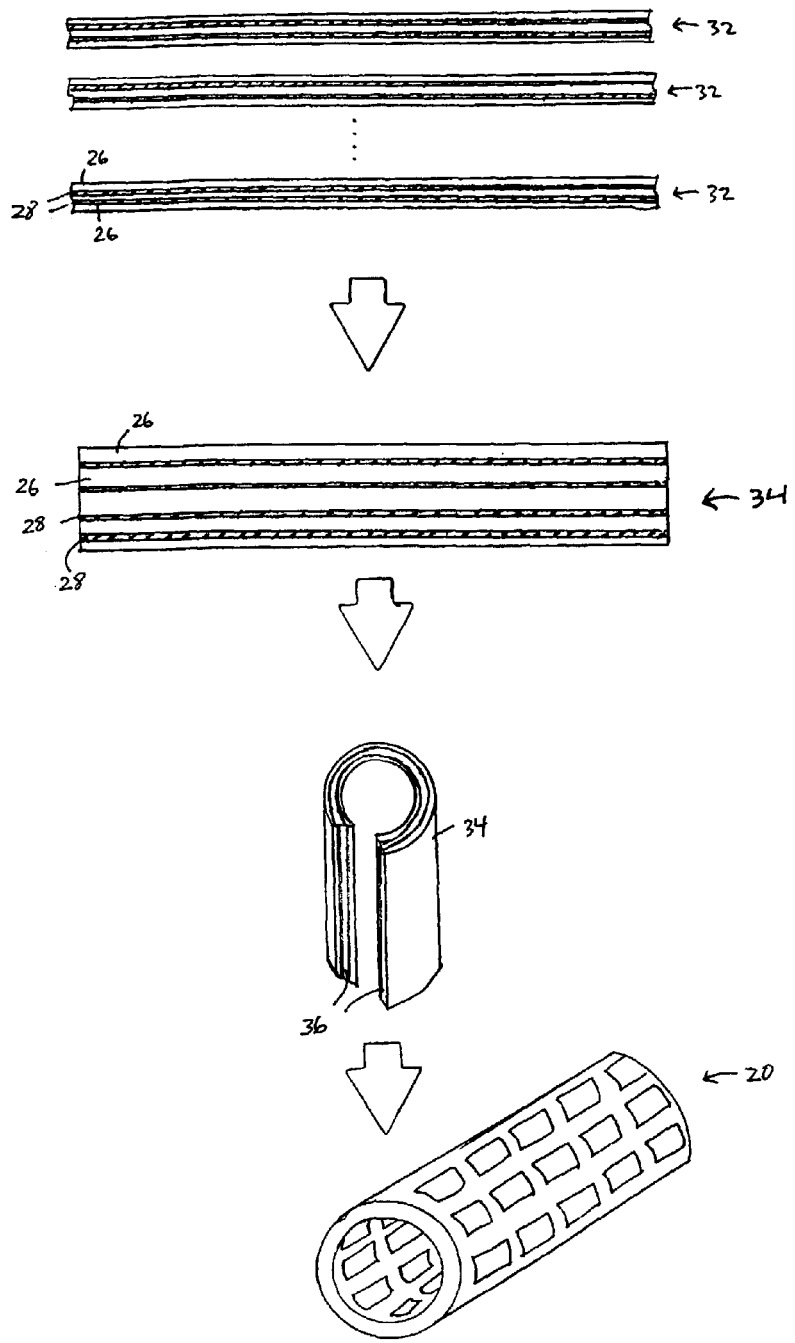
FIG. 3 illustrates an embodiment of a method of making a medical device.

Tubular body 22 can be formed by layering multiple layers or films of the composite material. Referring to FIG. 3, a method of making stent 20 is shown. Multiple layers 32 of the composite material can be formed according to the techniques described above. As shown, layers 32 have a lamellar structure, but the layers can have any structure of the composite material. In some embodiments, the layers can have different structures. For example, a layer can have a lamellar structure, and another layer can have a hexagonal structure. Layers 32 are then laminated together to form a sheet 34, e.g., one having a predetermined final thickness. Layers 32 can be laminated by pressing the layers under sufficient pressure, with or without heating the layers; and/or by applying an adhesive between the layers that is compatible with organic and inorganic portions 26 and 28. After lamination, sheet 34 can be cut to a selected size, e.g., length and width. Tubular body 22 is formed by rolling sheet 34 to bring opposing edges 36 of the sheet together, and joining the edges, e.g., using an adhesive and/or heating. In other embodiments, no lamination of the composite material is necessary, e.g., if one layer 32 is sufficiently sized. In some embodiments, sheet 34 is rolled, without joining opposing edges 36. Stent 20 can be expanded by an unrolling action.

In certain embodiments, an adhesion enhancing material can be incorporated into or applied to the composite material. An adhesion enhancing material can be used, for example, to enhance the adhesion between adjacent layers. Examples of adhesion enhancing materials include epoxy or anhydride modified polyolefins, such as LOTADER® (Elf Atochem) and KODAR® PETG (Eastman Kodak). The amount of adhesion enhancing material can vary depending upon the intended use. In certain embodiments, the adhesion between one or more adjacent layers can vary as layer thickness is varied.

Portions of tubular body 22 can be removed to provide an arrangement of openings 24. The portions can be removed by laser cutting, as described, for example, in U.S. Pat. No. 5,780,807. Alternatively or in addition, the portions can be removed by laser ablation, e.g., by using ultrashort pulses to reduce presence of debris. Laser ablation is described in U.S. Ser. No. 09/724,503, filed Nov. 28, 2000 and entitled "Method for Manufacturing A Medical Device Having A Coated Portion By Laser Ablation"; and M. Mendes et al., "Femtosecond UV Laser Micromachining of $Al_2O_3$—TiC", Proc. ICALEO 1999.

In other embodiments, a mold, such as one having a clamshell design, can be used to form tubular body 22. For example, rather than transferring the mixture described above into a petri dish, the mixture can be transferred into a tubular cavity defined by two or more removable elements to form a tubular body. Openings 24 can be formed in the tubular body as described above. In some embodiments, the mold can be designed such that the cavity of the mold defines a stent, and the mixture forms the shape of the stent directly.

In some embodiments, the composite material can form one or more layers of a multilayer medical device, such as a stent or a stent-graft. For example, selected layers of the stent or stent-graft can include the composite material, while selected layers can include a polymer material. The layers can alternate in arrangement. The composite material can be the innermost layer(s) and/or the outermost layer(s), although other arrangements are possible. Stents having a polymer material, e.g., with preferentially oriented fibers, and methods of making them are disclosed in U.S. Ser. No. 10/229,548, filed Aug. 28, 2002.

Stent 20 can be used, e.g., delivered and expanded, according to conventional methods. Suitable catheter systems are described in, for example, Wang U.S. Pat. No. 5,195,969, and Hamlin U.S. Pat. No. 5,270,086. Suitable stents and stent delivery are also exemplified by the Express® or Maverick® systems, available from Boston Scientific Scimed, Maple Grove, Minn.

Figure 4:
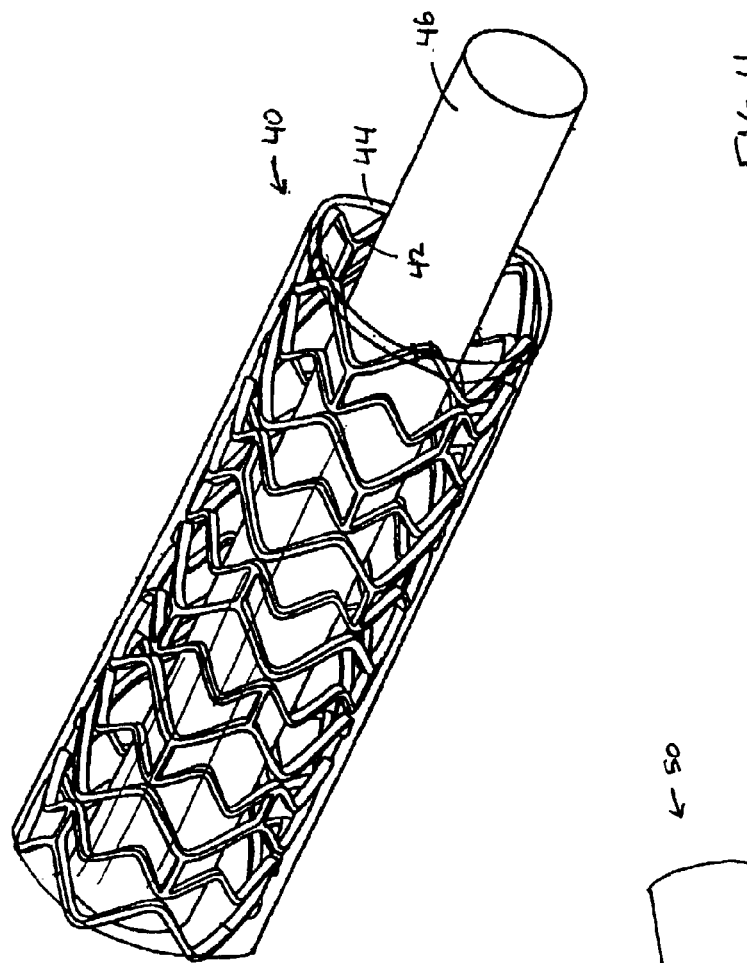
FIG. 4 is an illustration of an embodiment of a medical device.

In other embodiments, the composite material can be included in a stent-graft. Referring to FIG. 4, a stent-graft 40 includes a stent 42 and a composite material 44 carried by the stent. As shown, stent-graft 40 is positioned on a support 46, which can be, e.g., a catheter or a medical balloon, depending on the type of stent-graft. (For clarity, composite material 44 is shown as being transparent to show stent 42 and support 46. Composite material 44 can be opaque.) Stent 42 can be a balloon-expandable device, a self-expandable device, or a combination of both (e.g., as described in U.S. Pat. No. 5,366, 504). Composite material 44 is generally as described above, and can be attached to stent 42 by an adhesive and/or by mechanical pressing. In some embodiments, stent-graft 40 can include a stent placed between two or more layers of the composite materials. The layers can have the same structure or different structures. Composite material 44 can form one or more portions of a multilayer graft, as described above for stent 20.

In general, stent 20 and stent-graft 40 can be of any desired shape and size (e.g., coronary stents, aortic stents, peripheral stents, gastrointestinal stents, urology stents, and neurology stents). Depending on the application, stent 20 and stent-graft 40 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

In some embodiments, the composite material can have relatively large pores, e.g., when heated to high temperatures. The pores can facilitate stent 20 or stent-graft 40 having a releasable therapeutic agent or a pharmaceutically active compound, such as those described in U.S. Pat. No. 5,674, 242; commonly assigned U.S. Ser. No. 09/895,415, filed Jul. 2, 2001; U.S. Ser. No. 09/724,503; and U.S. Ser. No. 10/112, 391, filed Mar. 28, 2002. The therapeutic agents or pharmaceutically active compounds can include, for example, anti-thrombogenic agents, antioxidants, anti-inflammatory agents, anesthetic agents, anti-coagulants, and antibiotics. Alternatively or in addition, stent 20 or stent-graft 40 can include and/or be attached to a biocompatible, non-porous or semi-porous polymer matrix made of polytetrafluoroethylene (PTFE), expanded PTFE, polyethylene, urethane, or polypropylene. The polymer matrix can be attached to, e.g., layered with, the composite material.

In some embodiments, one or more preselected portions of the material can be heated locally (e.g., by using focused microwave radiation of about 2 to about 120 GHz, which can cause volumetric heating) to form the pores, while other portion(s) of the material are kept unheated (e.g., cooled by forced gas). The heated, porous portion(s) can be loaded with one or more drugs as described above to provide drug delivery to selected areas. The unheated, non-porous portion(s) can enhance the properties, e.g., mechanical properties, of the device.

Figure 5:
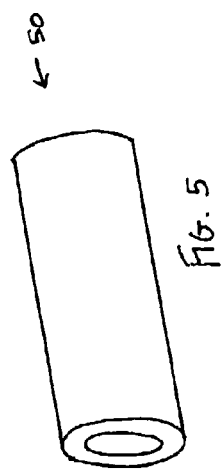
FIG. 5 is an illustration of an embodiment of a medical device.

The composite material can be used in other medical devices. For example, the composite material can be included in a medical balloon, e.g., an angioplasty balloon; a filter; or a balloon catheter. Examples of devices suitable for use with MRI are described in U.S. Ser. No. 10/216,988, filed Aug. 12, 2002. The composite material can be included in a vascular graft 50 (FIG. 5), e.g., described in U.S. Pat. No. 6,428,571. Tubular body 22 can be used as a medical tubing, e.g., as a catheter body.

All publications, references, applications, and patents referred to herein, including references cited therein, are incorporated by reference in their entirety.

Other embodiments are within the claims.

What is claimed is:

1. A device, comprising:
 a tubular body including a composite material, the composite material having a
 mesostructure comprising an organic portion, and an inorganic portion distinct from the organic portion, wherein the device is a medical device.

2. The device of claim 1, wherein the composite material comprises a plurality of organic portions and a plurality of inorganic portions distinct from the organic portions, the inorganic portions being in an ordered array.

3. The device of claim 2, wherein in the inorganic portions are lamellar.

4. The device of claim 2, wherein the organic portions are lamellar.

5. The device of claim 1, wherein the inorganic portion comprises a metallic element.

6. The device of claim 5, wherein the element is selected from a group consisting of silicon and aluminum.

7. The device of claim 1, wherein the inorganic portion comprises a three-dimensional network of metallic elements connected by bridging elements.

8. The device of claim 7, wherein the bridging elements comprise oxygen.

9. The device of claim 1, wherein the organic portion comprises a polymer.

10. The device of claim 1, wherein the organic portion comprises a block copolymer.

11. The device of claim 1, wherein the organic portions are about 5 to 100 nm long.

12. The device of claim 1, wherein the body further comprises a therapeutic agent.

13. The device of claim 1, wherein the composite comprises an adhesion enhancing material.

14. The device of claim 1, in the form of a stent.

15. The device of claim 1, wherein the body comprises a plurality of organic portions and a plurality of inorganic portions distinct from the organic portions, the inorganic portions being in an ordered array.

16. A device, comprising:
 a tubular body having a mesostructure comprising an organic portion, and an inorganic portion distinct from the organic portion, wherein the device is a stent.

* * * * *

UNITED STATES PATENT AND TRADEMARK OFFICE
CERTIFICATE OF CORRECTION

PATENT NO. : 8,449,601 B2
APPLICATION NO. : 10/299466
DATED : May 28, 2013
INVENTOR(S) : Jan Weber It is certified that error appears in the above-identified patent and that said Letters Patent is hereby corrected as shown below:

1.) Title Page, Section "Other Publications", Line 1 in section: delete "Alununosilicate" and insert --Aluminosilicate--.

2.) Title Page, Section "Other Publications", Line 9 in section: delete "$Al_2O_3$" and insert --$Al_2O_3$--.

Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

| | |
|---|---|
| PATENT NO. | : 8,449,601 B2 |
| APPLICATION NO. | : 10/299466 |
| DATED | : May 28, 2013 |
| INVENTOR(S) | : Jan Weber |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2175 days.

Signed and Sealed this
Twenty-seventh Day of January, 2015

Michelle K. Lee
*Deputy Director of the United States Patent and Trademark Office*